United States Patent [19]
McCoy et al.

[11] Patent Number: 5,702,684
[45] Date of Patent: Dec. 30, 1997

[54] METHOD OF USE OF COMPOSITIONS OF BIOCIDES AND FLUORESCENT INDICATORS TO CONTROL MICROBIAL GROWTH

[75] Inventors: William F. McCoy, Naperville; John E. Hoots, St. Charles, both of Ill.

[73] Assignee: Nalco Chemical Company, Naperville, Ill.

[21] Appl. No.: 557,882

[22] Filed: Nov. 14, 1995

Related U.S. Application Data

[63] Continuation-in-part of Ser. No. 236,945, May 2, 1994, abandoned.

[51] Int. Cl.$^6$ .............................. A61K 49/00; C02F 1/00
[52] U.S. Cl. .............................. 424/10.3; 422/3; 422/28; 422/37; 422/40; 210/745
[58] Field of Search .............................. 424/10.3; 422/3, 422/28, 37, 40; 210/745

[56] References Cited

U.S. PATENT DOCUMENTS

| | | | |
|---|---|---|---|
| 4,242,602 | 12/1980 | Nakagawa et al. | 307/232 |
| 4,783,314 | 11/1988 | Hoots et al. | 422/3 |
| 4,802,994 | 2/1989 | Mouché et al. | 210/759 |
| 4,966,711 | 10/1990 | Hoots et al. | 210/697 |
| 4,992,380 | 2/1991 | Moriarty et al. | 436/55 |
| 5,006,311 | 4/1991 | Hoots et al. | 422/62 |
| 5,041,386 | 8/1991 | Pierce et al. | 436/80 |
| 5,128,419 | 7/1992 | Fong et al. | 525/351 |
| 5,132,096 | 7/1992 | Hoots et al. | 422/82.09 |
| 5,166,074 | 11/1992 | Vessey et al. | 436/103 |
| 5,171,450 | 12/1992 | Hoots | 210/701 |
| 5,413,719 | 5/1995 | Sivakumar et al. | 210/708 |

FOREIGN PATENT DOCUMENTS

| | | |
|---|---|---|
| 0 466 303 A2 | 4/1991 | European Pat. Off. . |
| 55-003668 | 1/1980 | Japan . |

*Primary Examiner*—Sandra E. Saucier
*Attorney, Agent, or Firm*—Robert A. Miller; James J. Drake

[57] ABSTRACT

A concentration of microbiocides added to fluid systems is monitored by a fluorescence emission method which is based upon the measurement of the fluorescence intensity of an inert fluorescent additive which is added to the microbiocide composition prior to its introduction into the fluid system. Optionally, the fluorescent additive may be metered separately into the fluid system in direct proportion to the amount of industrial microbiocide added. Biocide compositions containing inert fluorescent additives are also disclosed. Preferably the fluid system is an industrial aqueous system. Preferred combinations of biocide and fluorescent additive are glutaraldehyde/1,5-naphthalene disulfonic acid, glutaraldehyde/1,3,6,8-pyrene tetrasulfonic acid, isothiazolone/1,5-naphthalene disulfonic acid, isothiazolone/1,3,6,8-pyrene tetrasulfonic acid, glutaraldehyde/fluorescein, alkyl-dimethylbenzyl ammonium chloride quaternary/2-naphthalene sulfonic acid and 2-(decylthio)-ethanamine/2-naphthalene sulfonic acid.

18 Claims, 4 Drawing Sheets

5,702,684

METHOD OF USE OF COMPOSITIONS OF BIOCIDES AND FLUORESCENT INDICATORS TO CONTROL MICROBIAL GROWTH

The present application is a continuation-in-part of application Ser. No. 08/236,945, filed on May 2, 1994 by William F. McCoy and John E. Hoots entitled "Compositions of Fluorescent Biocides for Use as Improved Antimicrobials", now abandoned, the disclosure of which is incorporated herein by reference.

TECHNICAL FIELD OF THE INVENTION

The present invention is in the technical field of microbiocide compositions and methods for monitoring and controlling the dosage of microbiocide compositions in fluid systems.

BACKGROUND OF THE INVENTION

Microbiocides are added to aqueous systems in a variety of industrial and recreational applications. Some of these applications include the addition of microbiocides to control the growth of algae, bacteria, fungi and protozoa in industrial cooling water systems, recreational water systems such as pools and spas, the addition of microbiocides to control bacteria in the manufacture of paper, the use of microbiocides to control bacterial growth during the processing of raw sugar, and the like. The invention may also find utility in the application of biocides used to control invertebrates including but not limited to zebra mussels, blue mussels, and Asiatic clams in industrial and municipal water intake systems and industrial cooling water systems. While particularly applicable to aqueous systems, the invention may also find utility in non-aqueous systems. As used herein, the terms "microbiocide" and "biocide" are used interchangeably and are meant to include chemicals used to control "pests" as defined under the Federal Insecticides Fungicide and Rodenticide Act (FIFRA) in both aqueous and non-aqueous fluid systems.

Current methods for the direct determination of the mount of microbiocide present in a fluid system tend to be time consuming measurements of the mount of bacterial growth in the system or wet-chemical analysis of samples for active microbiocide. These methods include culturing a sample taken from the fluid system to determine bacterial growth. If bacterial growth is present, more microbiocide is generally fed into the system until a culture shows a steady or decreasing mount of microbiological growth. Wet chemical analysis methods are time consuming, labor intensive and subject to great error when conducted in the field rather than a well equipped laboratory. Until the time of making this invention there has existed no convenient field method to rapidly and accurately determine the mount of microbiocide fed into a system. This invention is directed to microbiocide compositions or systems containing microbiocide having added thereto a small quantity of inert fluorescent tracer material in an amount proportional to the quantity of microbiocide so that the amount of microbiocide in the system can be measured on a continuous real-time basis by determining the level of fluorescence of the additive added to the microbiocide. In a preferred embodiment of this invention the fluid system is an aqueous system.

The use of tracer materials to monitor the effect of treatment chemicals such as corrosion and scale inhibitors in industrial water systems is well-known. Hoots U.S. Pat. No. 4,783,314 discloses the use of inert transition metal tracer materials for monitoring the concentration of corrosion and scale inhibitors using fluorometry. Hoots et al U.S. Pat. No. 4,966,711 and U.S. Pat. No. 5,041,386 teaches the use of inert fluorescent additives which are added in direct proportion to the amount of a corrosion and/or scale inhibitor to monitor the concentration of a corrosion and/or scale inhibitor in a given industrial water system. U.S. Pat. Nos. 4,992,380, 5,006,311, and 5,132,096 disclose methods and equipment to monitor fluorescent tracers used in industrial water treatment applications. U.S. Pat. Nos. 5,128,419 and 5,171,450 disclose water soluble polymers having fluorescent moieties that are used to monitor their concentration in industrial water treatment applications. Japanese Patent No.55003668 (1980) discloses an atomic adsorption spectroscopy method for monitoring biocide concentrations by adding and measuring lithium salt materials to indirectly determine the concentration of microbiocides. This method requires the separate addition of tracer material and requires the use of atomic adsorption spectroscopy to obtain results. Atomic adsorption spectroscopy is relatively expensive compared to fluorometry and has the additional disadvantage that atomic adsorption spectroscopy is not readily adaptable to field use due to the complex equipment involved, as well as open flame and flammable gas supplies.

U.S. Pat. No. 4,242,602 discloses an ultraviolet spectroscopy technique to monitor multiple water treatment components. The method involves the use of expensive analytical equipment along with computer hardware having specially written software. In addition, equipment must be calibrated on a site specific basis and recalibration may be necessary if conditions in the water change. European Patent Application 466303 discloses a method involving the addition of a substance to treated water and how it reacts with the microbiocide. The substance reacting with the microbiocide is continuously measured and the concentration of the microbiocide is determined by loss of the substance. The method is cumbersome, requires special equipment, and two separate chemical feeds.

The subject invention solves many of the problems detailed above by providing an easy to use, accurate, continuous method for the determination of microbiocide concentration in fluid systems, particularly industrial water systems.

OBJECTS OF THE INVENTION

It is an object of our invention to provide to the art industrial microbiocidal compositions useful for the control of bacteria, fungi, protozoa, invertebrates and algae in fluid systems, and more particularly, industrial water systems, which compositions can be measured continuously in the system to which they are added by fluorescent measurement means.

Another object of this invention is to provide to the art novel fluorescent microbiocidal compositions that can be conveniently, rapidly and continuously monitored in the fluid system to which they are added using relatively simple industrial monitoring equipment.

A further object of this invention is to provide to the art novel fluorescent biocide compositions and methods for the measurement and concentration maintenance of such microbiocide compositions.

A still further object of this invention is to provide to the art novel fluorescent biocide compositions and methods for the measuring system consumption of microbiocide.

Further objects will appear hereinafter.

THE INVENTION

Figure 1:
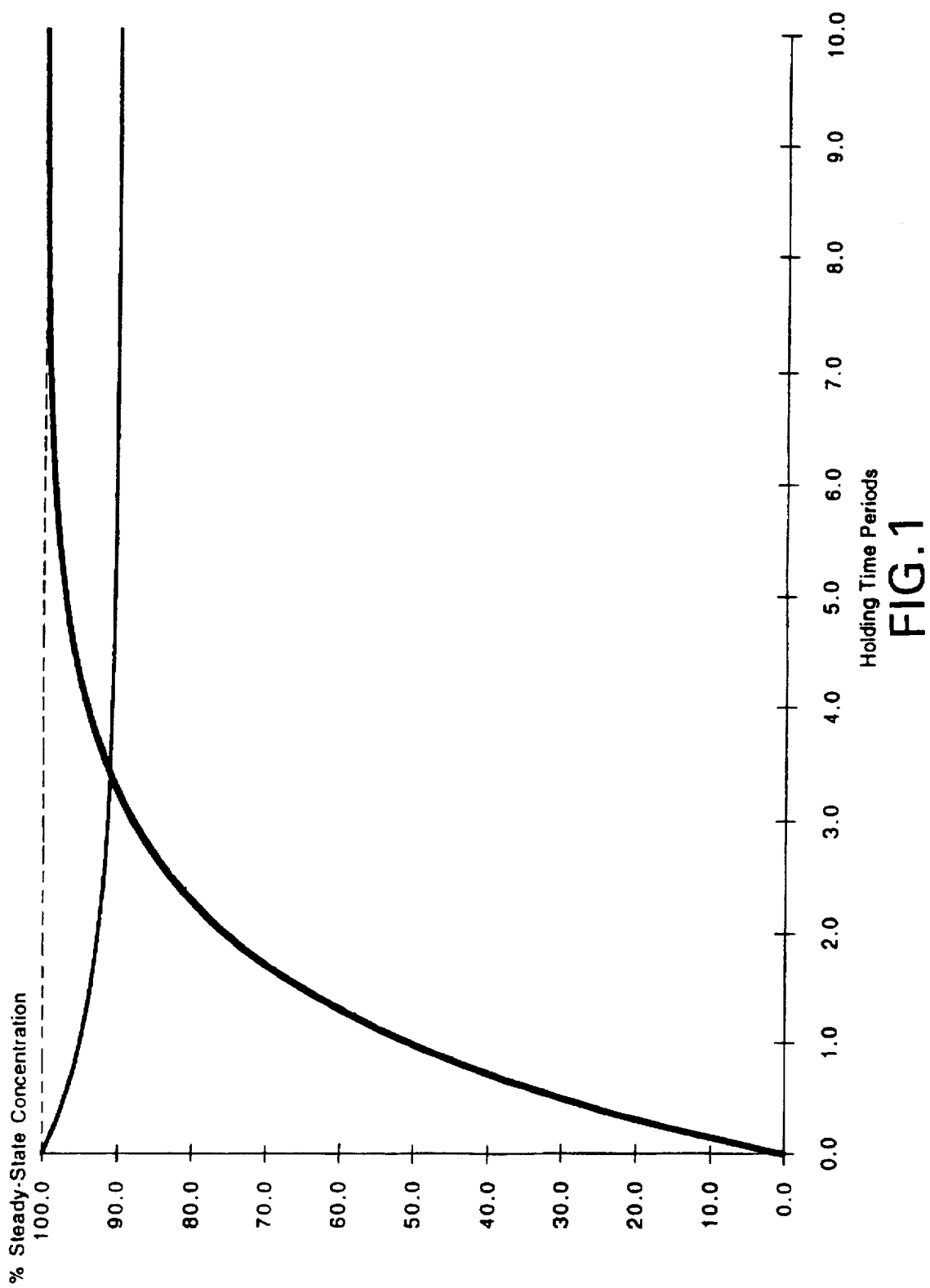
FIG. 1 represents the concentration of active biocidal ingredients in an industrial cooling tower as a function of holding time period where the biocide, but not the fluorescent tracer material, is partially or totally depleted.

The invention is a microbiocide composition for controlling the growth of microbiological organisms, the concentration of which when added to a fluid system containing said microbiological organisms is adapted to be measured in the system by the fluorescence level in said system of a fluorescent compound added in known proportion to the microbiocide, the composition comprising:

a) diluent;

b) microbiocide/inert fluorescent compound combination selected from the group consisting of glutaraldehyde/1,5 naphthalene disulfonic acid, glutaraldehyde/1,3,6,8 pyrene tetrasulfonic acid, isothiazolone/1,5 naphthalene disulfonic acid, isothiazolone/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active microbiocide.

The terms 1, 3, 6, 8 pyrene tetrasulfonic acid; 1,5 naphthalene disulfonic acid and 2-naphthalene sulfonic acid as used herein are meant to also encompass the salts of the sulfonic acids, for example, the disodium salt of 1,5 naphthalene disulfonic acid. The term fluorescein as used herein is meant to encompass salts of fluorescein, for example, fluorescein potassium salt.

The term alkyl dimethyl benzyl ammonium chloride refers to a compound which has a mixture of $C_{12}$-$C_{16}$ n-alkyl groups.

Preferably, from 0.005 to 2.0 percent by weight of the inert fluorescent compound is added based on the weight of active microbiocide, and most preferably from 0.025 to 1.0 percent by weight of the inert fluorescent compound is added based on the weight of active microbiocide. The inert fluorescent compound may be soluble or evenly dispersible in the diluent, wherein said diluent may be water and the composition may be added to an aqueous system.

Additionally, the invention is a method for controlling the feed of an aqueous biocide for controlling growth of microbiological orgasms into an aqueous system containing said microbiological organisms which comprises:

a) adding said system a known amount of a microbiocide/ inert fluorescent compound combination is elected from the group consisting of glutaraldehyde/1,5 naphthalene disulfonic acid, glutaraldehyde/1,3,6,8 pyrene tetrasulfonic acid, isothiazolone/1,5 naphthalene disulfonic acid, isothiazolone/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active microbiocide in a weight ratio of active microbiocide to tracer of from 3:1 to 1000:1, said microbiocide being added at a level to provide a system having a biocide dosage at or slightly greater than the minimum inhibitory concentration for said microbiocide in the system;

b) measuring the fluorescence of said microbiocide at or slightly above the minimum inhibitory concentration of said microbiocide; and c) maintaining the fluorescence in the system at a constant rate equal to the fluorescence at or slightly greater than the minimum inhibitory concentration of the microbiocide by adding additional microbiocide as required.

Preferably, from 0.005 to 2 percent by weight of the inert fluorescent compound is added based on the weight of active microbiocide. More preferably, from 0.025 to 1.0 percent by weight of the inert fluorescent compound is added based on the weight of active microbiocide.

The measurement of the fluorescence of the microbiocide may be continuously monitored by a fluorometer. That fluorometer signals a microbiocide feed pump to turn on in response to levels of fluorescence below a set treatment level, and signals the pump to turn off in response to levels of fluorescence above a set treatment level. The aqueous system is selected from the group consisting of recreational water systems, paper mill white water systems, industrial water systems and open recirculating cooling systems. Industrial water systems may include air washer systems, once-through systems and humidification systems.

Another embodiment of the invention is a method for determining the consumption of microbiocide for controlling growth of microbiological organisms within a fluid system containing said microbiological organisms which comprises:

a) adding to said fluid system containing microbiological organisms a microbiocide/inert fluorescent compound combination selected from the group consisting of glutaraldehyde/1,5 naphthalene disulfonic acid, glutaraldehyde/1,3,6,8 pyrene tetrasulfonic acid, isothiazolone/1,5 naphthalene disulfonic acid, isothiazolone/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active microbiocide;

b) determining the amount of biocide originally added to the system by measuring the fluorescence of the fluorescent compound present in the system;

c) determining the amount of biocide present in the system; and d) subtracting the actual amount of biocide present as determined in step (c) from the total amount of biocide added as determined in step (b) and calculating biocide consumption.

Preferably, from 0.005 to 2 percent by weight of the inert fluorescent compound is added based on the weight of active microbiocide. More preferably, from 0.025 to 1.0 percent by weight of the inert fluorescent compound is added based on the weight of active microbiocide.

The system may be an aqueous system. The inert fluorescent compound may be added to the biocide at a level to obtain a 0.005 to 1.0% weight percent of the fluorescent compound. The aqueous system is selected from the group consisting of recreational water systems, paper mill white water systems, industrial water systems and open recirculating cooling systems.

Furthermore, the invention is a method for maintaining the concentration of a microbiocide for controlling growth of microbiological organisms in an industrial fluid system containing said microbiological organisms within present limits which comprises:

a) adding to said industrial fluid system containing microbiological organisms a microbiocide/inert fluorescent compound combination selected from the group consisting of glutaraldehyde/1,5 naphthalene disulfonic acid, glutaraldehyde/1,3,6,8 pyrene tetrasulfonic acid, isothiazolone/1,5 naphthalene disulfonic acid, isothiazolone/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active microbiocide;

b) determining the amount of microbiocide originally added to the system by measuring the fluorescence of the inert fluorescent compound present in the system;

c) determining the amount of microbiocide present in the system; and d) subtracting the actual amount of microbiocide present as determined in step (c) from the total amount of biocide added as determined in step (b) and calculating the amount of biocide consumed; and e) adding to the industrial fluid system an amount of microbiocide to maintain the biocide at a specified minimum inhibition concentration.

Preferably, from 0.005 to 2 percent by weight of the inert fluorescent compound is added based on the weight of active microbiocide. More preferably, from 0.025 to 1.0 percent by weight of the inert fluorescent compound is added based on the weight of active microbiocide.

The industrial fluid system may be an aqueous system.

The inert fluorescent compound is added to the microbiocide at a level to obtain a 0.005 to 1.0% weight percent of the fluorescent compound based on microbiocide active ingredients. The aqueous system is selected from the group consisting of recreational water systems, paper mill white water systems and open recirculating cooling systems.

As stated earlier, it is an object of this invention to provide to the art novel fluorescent microbiocide concentrations, the concentrations of which can be conveniently and continuously measured, using industrial fluorometers. In addition, based upon fluorescent readings, the control of the addition of the microbiocide may be started or stopped depending upon the reading obtained. Basic compositions of this invention include the addition of 0.0005 to 10.0% by weight of an inert organic fluorescent substance (as active) to a microbiocide (as active). Preferably from 0.005 to 2.0% and most preferably 0.025 to 1.0% by weight of the fluorescent organic compound is added based on the weight of the active microbiocide. As seen from the scope of the above weight percents, it is not critical that either a lower, or an upper limit of the fluorescent compound be present based on the biocide, all that is important is that the fluorescent material be present in the microbiocide composition at a level where k may be detected by fluorescence measuring means at the use concentrations to which the microbiocide is employed. Thus, the weight ratio of the active microbiocide material to fluorescent material may range from 3:1 to 1000:1. Higher levels of fluorescent material may be used, but are generally uneconomical and unnecessary.

The inert fluorescent compounds may be selected from a wide variety of materials. Basic considerations that should be taken into account in selecting the inert fluorescent compounds are that they should be:

1. substantially inert to the active microbiocide ingredients into which they are to be added;

2. substantially inert to the system into which the industrial microbiocide is to be added; and 3. fluoresce at a wave length that is distinguishable from the wave length of other compounds that may be added to the system.

4. be soluble, or uniformly suspended, in the diluent containing the microbiocide.

In addition to the above, the fluorescent compounds should be soluble or evenly dispersible in the fluid systems to which they are added at the concentration levels employed.

If intended for use in dilute aqueous systems, the fluorescent compounds should be substantially water-soluble at the concentration levels employed.

Examples of fluorescent compounds which may be employed in this invention include the following: mono-, di- and trisulfonated naphthalenes, including their water soluble salts, particularly the various naphthalene mono-and disulfonic acid isomers, which are preferred inert tracers for use in the present invention. The naphthalene mono- and disulfonic acid isomers are water-soluble, generally available commercially and are easily detectable and quantifiable by known fluorescence analysis techniques. Preferred naphthalene mono- and disulfonic acid isomers are the water-soluble salts of naphthalene sulfonic acid ("NSA"), such as 1-NSA and 2-NSA, and naphthalene disulfonic acid ("NDSA" or "NDA"), for instance 1,2-NDSA, 1,3-NDSA, 1,4-NDSA, 1,5-NDSA, 1,6- NDSA, 1,7-NDSA, 1,8-NDSA, 2,3-NDSA, 2,4-NDSA and so forth. Many of these inert tracer(is) (mono-, di-, and trisulfonated naphthalene and mixtures thereof) are generally compatible with the environments of most aqueous systems employing industrial microbiocides. Among these preferred fluorescent tracers, 2-NSA and 1,5-NDSA have been found to be thermally stable (substantially inert) at temperatures up to at least about 540° C. (1004° F.), for at least 24 hours at 285° C. (545° F.) at pressures up to about 1,500 psig for time periods at least commensurate with, and often well in excess of, commercial water system holding times. Such inert fluorescent tracers are not volatized into steam.

Another group of inert fluorescent tracers that are preferred for use in the process of the present invention are the various sulfonated derivatives of pyrene, such as 1,3,6,8-pyrene tetrasulfonic acid, and the various water-soluble salts of such sulfonated pyrene derivatives. Many other water soluble tracer materials that fluoresce will be apparent to those skilled in the art. As a general rule, and in the selection of tracers for the traced biocides of this invention, tracers should be:

1. Thermally stable and not decompose at the temperature within the given system to which industrial microbiocides are fed;

2. Detectable on a continuous or semicontinuous basis and susceptible to concentration measurements that are accurate, repeatable, and capable of being performed on the system to which the industrial microbiocides are fed;

3. Substantially foreign to the chemical species that are normally present in the water to which the industrial microbiocides are fed;

4. Substantially impervious to any of its own potential specific losses from the water of the system to which the industrial microbiocides are fed;

5. Substantially impervious to interference from, or biasing by, the chemical species that are normally present in the water to which the industrial microbiocides are added;

6. Compatible with all treatment agents employed in the system in which the inert tracer may be used, and thus in no way reduce the efficacy thereof;

7. Compatible with all mechanical components of the system to which the industrial microbiocide is to be added, and be stable in the microbiocide formulations during any storage and transportation conditions encountered; and, 8. Reasonably nontoxic and environmentally safe, not only within the system to which the microbiocide is added, but also upon discharge therefrom.

The compositions and methods of this invention are applicable to both so-called non-oxidizing and oxidizing microbiocides. Examples of commonly available oxidizing biocides to which this invention may find utility include but are not limited to the following: hypochlorite bleach, hydrogen peroxide, peracetic acid, potassium monopersulfate, bromochlorodimethylhydantoin, dichloroethylmethylhydantoin, and chloroisocyanurate. The compositions and methods of this invention are also applicable to ingredients that later react to form biocidal compositions. Examples of materials of this type include the reaction of sodium bromide with chlorine to produce hypobromite bleach, a material more toxic than hypochlorite bleach to certain organisms.

Examples of commonly available non-oxidizing biocides to which this invention may find applicability include but are not limited to the following: dibromonitfilopropionamide, thiocyanomethylthiobenzothlazole, methyldithiocarbamate, tetrahydrodimethylthladiazonethione, tributyltin oxide, bromonitropropanediol, bromonitrostyrene, methylene bisthiocyanate, chloromethylisothlazolone, methylisothiazolone, benzisothlazolone, dodecylguanidine hydrochloride, polyhexamethylene biguanide, tetrakis (hydroxymethyl) phosphonium sulfate, glutaraldehyde, alkyldimethylbenzyl ammonium chloride, didecyldimethylammonium chloride, poly[oxyethylene-(dimethyliminio) ethylene (dimethyliminio) ethylene dichloride], decylthioethanamine, and terbuthylazine.

It is particularly preferred to formulate the fluorescent materials of this invention with the so-called isothiazolone materials such as those sold under the Kathon® trademark by Rohm and Haas Corporation, as well as glutaraldehyde and 2-(decylthio)ethanamine.

As used herein, the term biocide means any agent added to control pests including bacteria, fungi, algae, protozoa, and invertebrates in aqueous systems such as industrial and/or recreational water systems that require the control of pests.

A most preferred composition for use in this invention is a mixture of 99 weight percent of an isothiazolone biocide containing 1.5% active isothiazolones and 1.0% by weight of a 10% aqueous solution of 1, 3, 6, 8 pyrene tetrasulfonic acid (sodium salt).

The compositions of this invention are generally formulated by simply blending the selected inert organic fluorescent material with the microbiocide in amounts to provide a ratio of the fluorescent compound to active microbiocide in the ratios previously set forth.

If usage in an aqueous system is desired, the diluent for the fluorescent compound is preferably water. If usage is to be in a non-aqueous system, the diluent should be such that the fluorescent compound is soluble in the diluent, and both fluorescent compound and diluent should be miscible in the system. If, for example, the microbiocide employed is carried in a polyethylene glycol diluent, the fluorescent tracer materials of this invention must be soluble or evenly dispersible in the polyethylene glycol diluent.

If the biocide contained in the polyethylene glycol diluent is used in an aqueous system, the tracer so employed should also be readily soluble, or evenly dispersible in the aqueous system. If the biocide contained in the polyethylene glycol diluent is to be used in a non-aqueous system, the tracer selected should also be soluble, or at least evenly dispersible in the non-aqueous system.

By utilizing compositions of this invention, along with appropriate fluorescent measuring devices, an accurate and continuous method for determining the chemical concentration of microbiocide in applications such as, but not limited to, industrial water treatment and papermaking is achieved. The initial dose of the microbiocide to the system can be precisely, quickly, and inexpensively determined. Thus, an improvement in the art is provided by correcting the single most common misapplication of industrial biocides, namely, incorrect dosage of biocide added to the system.

Furthermore, the compositions and methods of this invention provide an important means to document and record the amount of product released into the environment from the industrial water system in order to manage the discharge of toxic compounds. Further, the invention provides means to minimize the dosage of product required to achieve microbiological control. The invention also provides a means to control the treatment regime, e.g. the frequency and amplitude of microbiocide dosage in order to improve the antimicrobial performance of the treatment. The inert tracer containing microbiocides of the subject invention are monitored much in the same way as disclosed in, e.g. U.S. Pat. No. 4,992,380 and U.S. Pat. No. 4,783,314, both of which are hereinafter incorporated by reference into the specification. The invention also allows for the determination of flow distribution of a biocide in a fluid system so as to be able to readily detect areas where biocide is not present, or is present in excess of concentration. The invention is also adaptable to allow determination of system biocide consumption.

One of the most useful features that this invention allows is the determination of biocide consumption in a system where the amount of biocide added to the system is not directly known. This method generally encompasses the following steps:

a) adding to such fluid system a microbiocide containing from 0.0005 to 10 weight percent of a substantially inert fluorescent compound;

b) determining the amount of biocide originally added to the system by measuring the fluorescence level of the fluorescent compound present in the system;

c) determining the amount of biocide present in the system by a known means; and d) Subtracting the actual amount of biocide present as determined in step (c) from the total amount of biocide added as determined in step (b) and calculating biocide consumption.

In the above description, it will be seen that a means other than measuring the fluorescence of the fluorescent compound should be utilized in step c. This method can be any one of a number of methods, including chromatography, wet chemical means or the like. Fluorescence may be measured to determine the total amount of biocide added. This method may be utilized over either a relatively short period of time, or a long period of system time so long as the tracer, the indicator of total biocide addition is not lost or decomposed.

The invention may also be employed to automatically add microbiocide into a system, thereby keeping the biocide at a level at or greater than its minimum inhibitory concentration. In this embodiment of the invention, the amount of biocide in the system is continuously determined by fluorescence measurement. In the event the fluorescence level decreases from a present known value, the fluorometer sends a signal to a controller, or to a pump to feed additional biocide until a proper fluorescence level is achieved. Means for allowing a fluorometer to send a signal to a pump, alarm device, or modem are generally known in the art, and will not be discussed herein. Additionally, biocide can be added to a system based upon the consumption measurement determined above by determining consumption, and then adding an amount of biocide to the fluid system in direct proportion to the amount consumed. This method can be used to keep the biocide level in a system at or slightly above the specified minimum inhibitory concentration of the biocide in the system.

In general, the concentration of the fluorescent tracer added to the microbiocide compositions of this invention is directly determined from a calibration curve of the tracer concentration vs. fluorescence emission. That comparison permits the determination of the concentration range over which linear emission response is observed. At higher tracer concentrations, a negative deviation from ideal behavior may be observed. The concentration of the tracer can still be determined directly from the calibration curve, or the sample can simply be diluted until the tracer concentration falls within the linear emission response range. For extremely dilute samples, techniques exist for increasing the concentration of the fluorescence tracer (e.g. liquid-liquid extraction) until it lies within the desirable concentration range. The compositions of this invention containing the fluorescent biocide materials are measured preferably by fluorometry. In this method, a sample of the system containing the biocide is excited by passing a light wave of known wave length into the sample. The wave length utilized is determined by the frequency at which the sample fluoresces, and if other constituents in the system also fluoresce at a known wave length after excitation at this frequency. After excitation of the sample, the emission caused by the excitation is measured. Fluorometers for this purpose are commercially available from a variety of sources. Preferred fluorometers for this purpose are available from the Nalco Chemical Company, Naperville, Ill. under the trade name TRASAR®.

In selecting an appropriate fluorescent reagent, wave length tables are readily available from chemical suppliers. If no table is available, simple measurements will determine acceptable wave lengths for excitation and measurement (emission).

By properly choosing the fluorescent reagent additive to the microbiocides of this invention, quantitative and in-situ measurement of tracer levels from parts per trillion to parts per million can be routinely accomplished on an instant or continuous basis with inexpensive portable equipment. While the above description has dealt with the addition of the fluorescent tracer material directly to the biocide, the fluorescent tracer may also, without departing from the spirit and intent of this invention, be added directly to the system in direct proportion to the amount of industrial microbiocide being fed into the system.

In the use of the compositions and measurement techniques of this invention to control microbiological and algae growth in aqueous systems, a brief description of the system is necessary.

The invention can be utilized in a broad range of aqueous, mixed aqueous/non-aqueous, or non-aqueous liquid systems (e.g. clarifiers, waste treatment, liquid-solid separations, down-hole oil field applications, papermills, cooling water systems, etc.) where the level of microbiocide present in the system affects performance of the system.

The systems to which this invention finds utility include industrial cooling water systems, recreational pools and spas, paper mill water, oil field production water, sugar beet processing and any other aqueous systems where biological growth must be controlled.

The fluorescent biocides of this invention also find utility in the prevention of microbiological growth in all kinds of aqueous systems including, but not limited to, foodstuffs, cosmetics, soaps, shampoos, etc. where the rapid determination of the amount of microbiocide present in such product is required for quality control or regulatory purposes.

In order to exemplify the invention, the following description is presented relative to the use of the microbiocide compositions of the invention in relation to an industrial open recirculating cooling water system.

Hoots, U.S. Pat. No. 4,783,314 which is hereinafter incorporated by reference into this specification discloses and discusses at length the use of tracer materials to monitor the concentration of scale and corrosion inhibitor ingredients in cooling water formulations. While microbiocides are consumed at a much more rapid rate than typical scale or corrosion inhibitor materials, the discussion in Hoots is incorporated herein as background as to how biocide materials containing tracer materials may be utilized in industrial water treatment applications.

The successful use of the traced industrial biocides of this invention enable the user to determine what happens if a system upset depletes the active ingredient but not the tracer (measures dosage of biocide added to system) contained in the active ingredient, and what happens as a result of continuous system consumption on the active ingredient.

FIG. 1 shows the concentration of active biocidal ingredient in an industrial cooling tower as a function of holding time period. The equation $\ln 2(V/F_s)=T$, (where V is the volume of the system, and $F_s$ represents the volumetric flow rate out of the system [blowdown & drift & leakage]). T represents the holding time of a biocide that has been continuously added to a well-mixed system with constant dilution rate and volume. The recovery to steady-state concentration after an upset in which the active biocide ingredient, but not fluorescent tracer, is partially or entirely depleted takes about 5 holding time periods. The actual concentration at steady-state will be lower than theoretically a factor of about 2 times the constant system demand on active ingredient.

Referring again to FIG. 1, in a system upset that preferentially deletes the active biocide ingredient, the concentration of the active ingredient ($C_s$) as a function of time can be represented by the equation:

$$C_s = (F_a/F_s)C_a[1-e^{-(F_s t/V)}]$$

where the volume is constant (dV/dt=0), $F_a$ is the volumetric flow rate of biocide into the system, $C_a$ is the concentration of active ingredient in the product, $F_s$ is the volumetric flow rate out of the system (e.g., blowdown & drift & leakage) and t is time. This expression is the integral of a first order differential equation based on the material balance around active ingredient concentration in a well-mixed system. The steady-state concentration of active ingredient will recover about 97% in approximately 5 holding periods. A plot of the equation is found in FIG. 1 where concentration is given as a function of the holding time period when holding time (T) is ln2(V/$F_s$).

The actual steady-state concentration will differ from the theoretical concentration when there is a preferential system consumption on the active ingredient. In such a circumstance, if the consumption is constant, the actual steady-state concentration of active ingredient will be lower than theoretical by a factor of about 2 times the consumption. For example, if the steady-state concentration is 100 mg/l and consumption is constant at 5 mg/l, then the actual steady-state concentration will be about 100 mg/l minus (2×5) mg/l or 90 mg/l. The general case is described by a geometric progression and limit analysis which reduces, in this case to:

$$C_s = C_a(F_a/F_s) - s(0.5^n - 1)/-0.5$$

where the volume is constant (Dv/dt=0), $C_a$ is the concentration of the active ingredient in the product, $F_a$ is the volumetric flow rate of the biocide into the system, $F_s$ is the volumetric flow rate out of the system (blowdown & drift & leakage), $C_a(F_a/F_s)$ is the concentration at steady-state with no consumption, s is the system consumption of active ingredient, and n is the number of holding time periods where holding time (T)=ln2(V/$F_s$). Conversely, the actual system consumption of the traced biocide can be accurately and easily measured by simply solving the equation for s, in the case where the steady-state concentration ($C_aF_a/F_s$) and the number of holding time periods (n) are known. The plot of this equation is indicated in FIG. 1 for the case where constant system consumption is 5%. This equation is indicated by the line that starts at 100% on the top left of the Figure. The plot starting at the lower left of FIG. 1 shows recovery after an upset in which all active ingredients are preferentially lost and subsequent system consumption is negligible.

In order to illustrate the subject invention, the following Examples are presented.

EXAMPLE I

A biocide composition containing a fluorescent indicator was made by blending 1 part by weight of a 10% by weight aqueous solution of 1,3,6,8-pyrene tetrasulfonic acid sodium salt into 80.72 parts water, 13.39 parts of Kathon® 886-F (a 14.1% by weight active solution of isothiazolone biocide available from Rohm & Haas, Philadelphia, Pa.), and 6.79 parts by weight of a 41.2 percent by weight aqueous solution of copper nitrate available from Shepard Chemical, Cincinnati, Ohio. The mixture was made by simple blending and contained 0.1 part as active of the pyrene tetrasulfonic acid material noted above.

EXAMPLE II

The material of Example 1 was fed into a commercial open recirculating cooling system in a refinery. The biocide containing the substantially inert fluorescent compound was added to the system and monitored by fluorometry and by liquid chromatography to determine the efficacy of fluorescent monitoring. The actual system consumption of biocide was minimal. Liquid chromatography requires expensive equipment, complicated methods, and long run times to get results. It is accordingly not a practical field method. As of the time this application was prepared, data shows good correlation between fluorescence measurements made in the field and liquid chromatography measurements made on specially preserved samples that were analyzed in a laboratory setting. The correlation between methods demonstrates that the invention provides a quick, simple, accurate and inexpensive field assay method. In the subject test, fluorescence measurements were taken on a Shadows can II fluorometer sold commercially by Nalco Chemical Company, Naperville, Ill. The fluorometer was operated at a wave length of 365 nm (excitation) and 400 nm (emission).

By operating with the traced biocide system, microbiological control of the cooling tower was improved over the slug feeding of microbiocides that had previously been employed.

Figure 2:
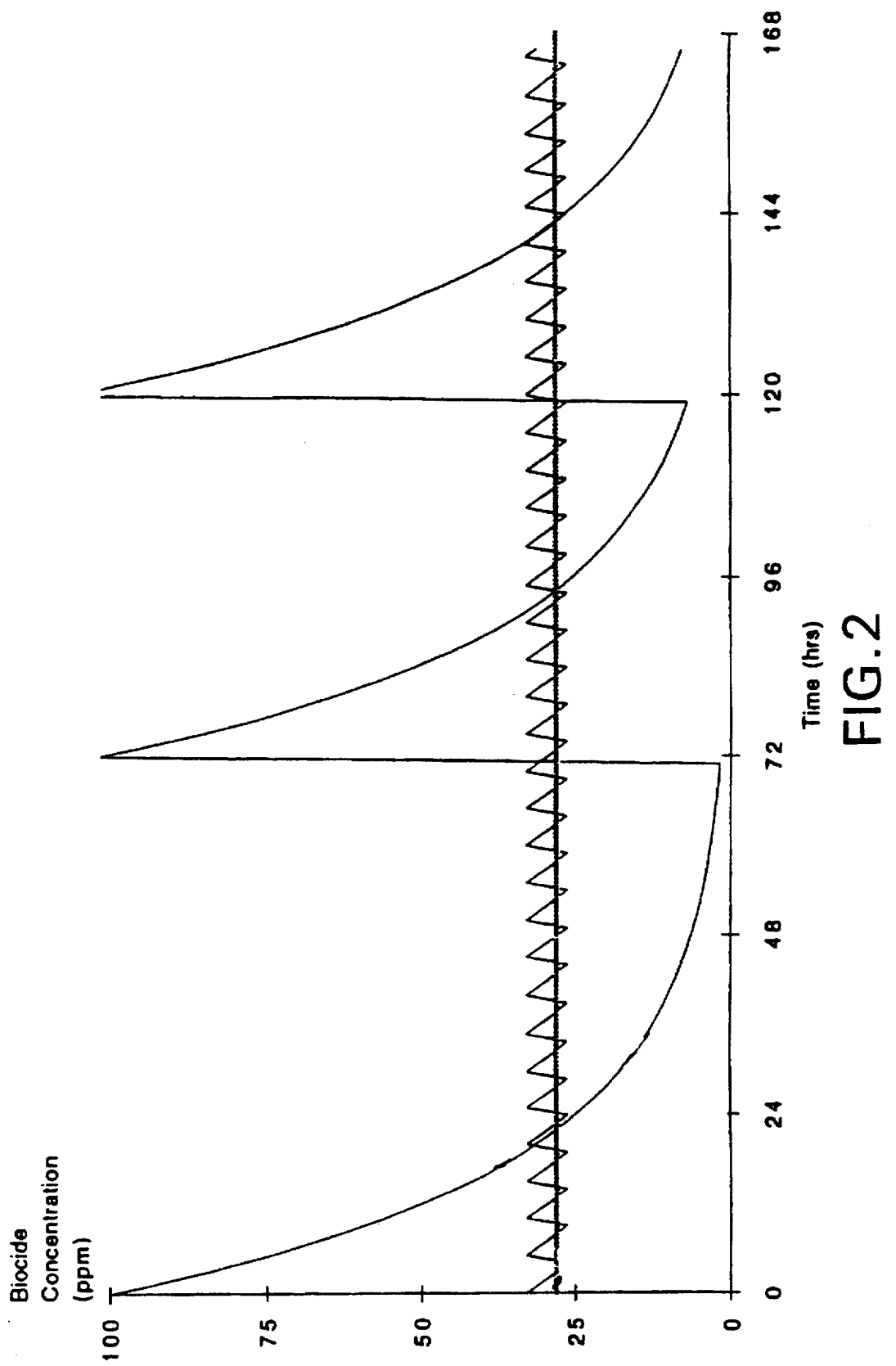
FIG. 2 represents a comparison of the control of an industrial cooling tower biocide program using the composition of this invention vs. slug feeding of the biocide.

FIG. 2 shows a comparison of the feed of the above noted biocide treatment. Nonoxidizing biocides are usually slug-dosed 2 or 3 times per week when used as the primary antimicrobial treatment. More frequent low-doses based on blowdown (cooling water discharge) or other dilution have not been considered practical because of the difficulty in measuring biocide concentration. Biocides work well when their concentrations are greater than their minimum inhibitory concentration, and are generally ineffective at concentrations below their minimum inhibitory concentrations. The minimum inhibitory concentration for the biocide in question, in the system treated was 25–30 ppm. As seen from the FIG. 2, the use of fluorometry to control concentration provides greater control of the system, and can provide continuous protection of systems from microbiocidal growth in comparison to slug-feeding which provided essentially no protection for a time period of 48 hours following the slug dose until the next slug-dose was delivered. In contrast, the fluorescent biocide treatment program provided a continuous, uninterrupted biocide feed to protect the system from microorganisms.

Figure 3:
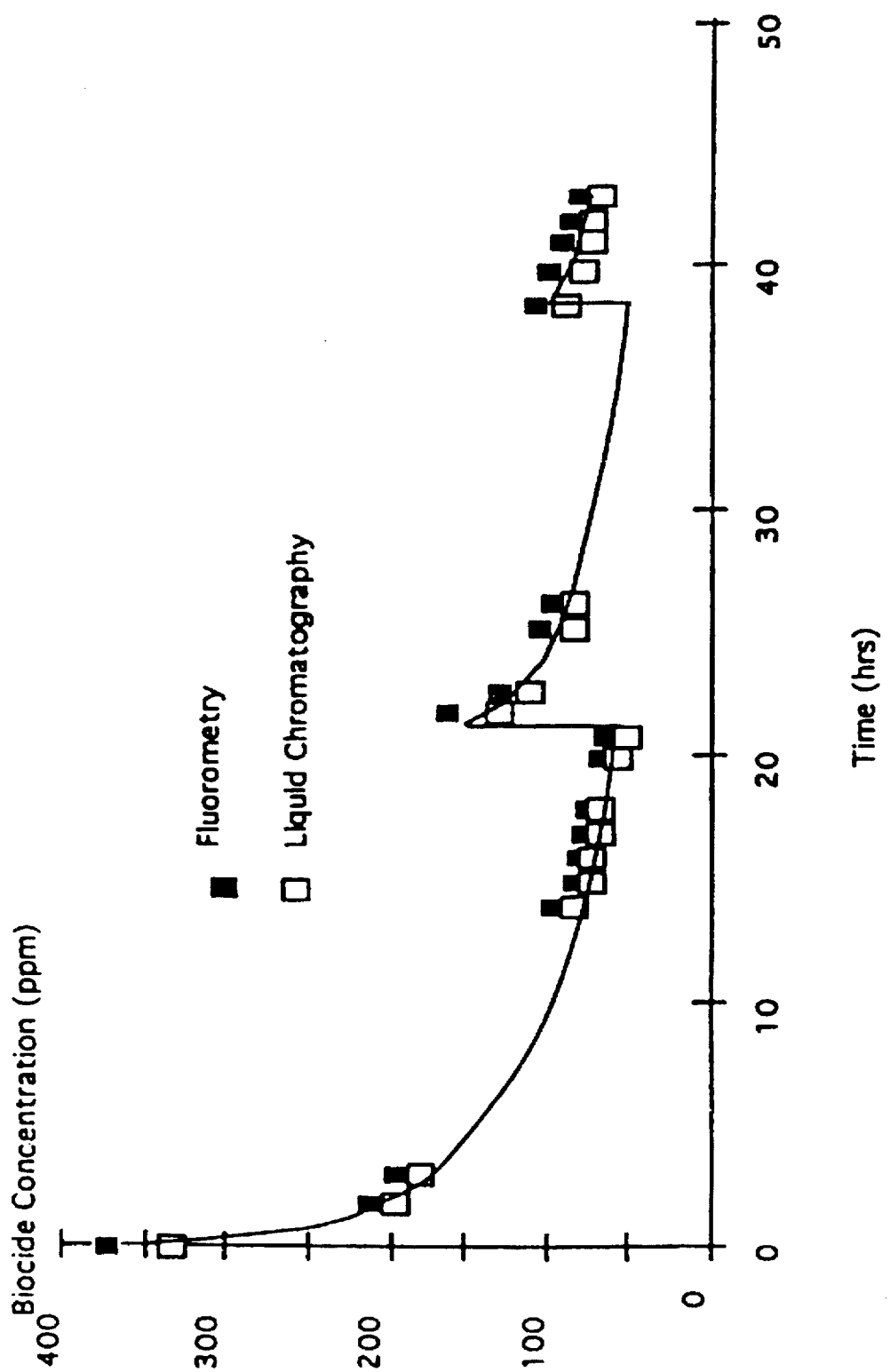
FIG. 3 represents the results of a microbiocide application showing the correlation of inert fluorescent compound (by fluorometry) and microbiocide active (by HPLC) during which slug-doses and continuous doses of product were used.

FIG. 3 shows the correlation between biocide concentrations as determined by liquid chromatography vs. the method of the subject invention. This study was conducted using this Example and shows the correlation between liquid chromatography and the subject invention over a two-day period, the data from which is given in FIG. 4.

Figure 4:
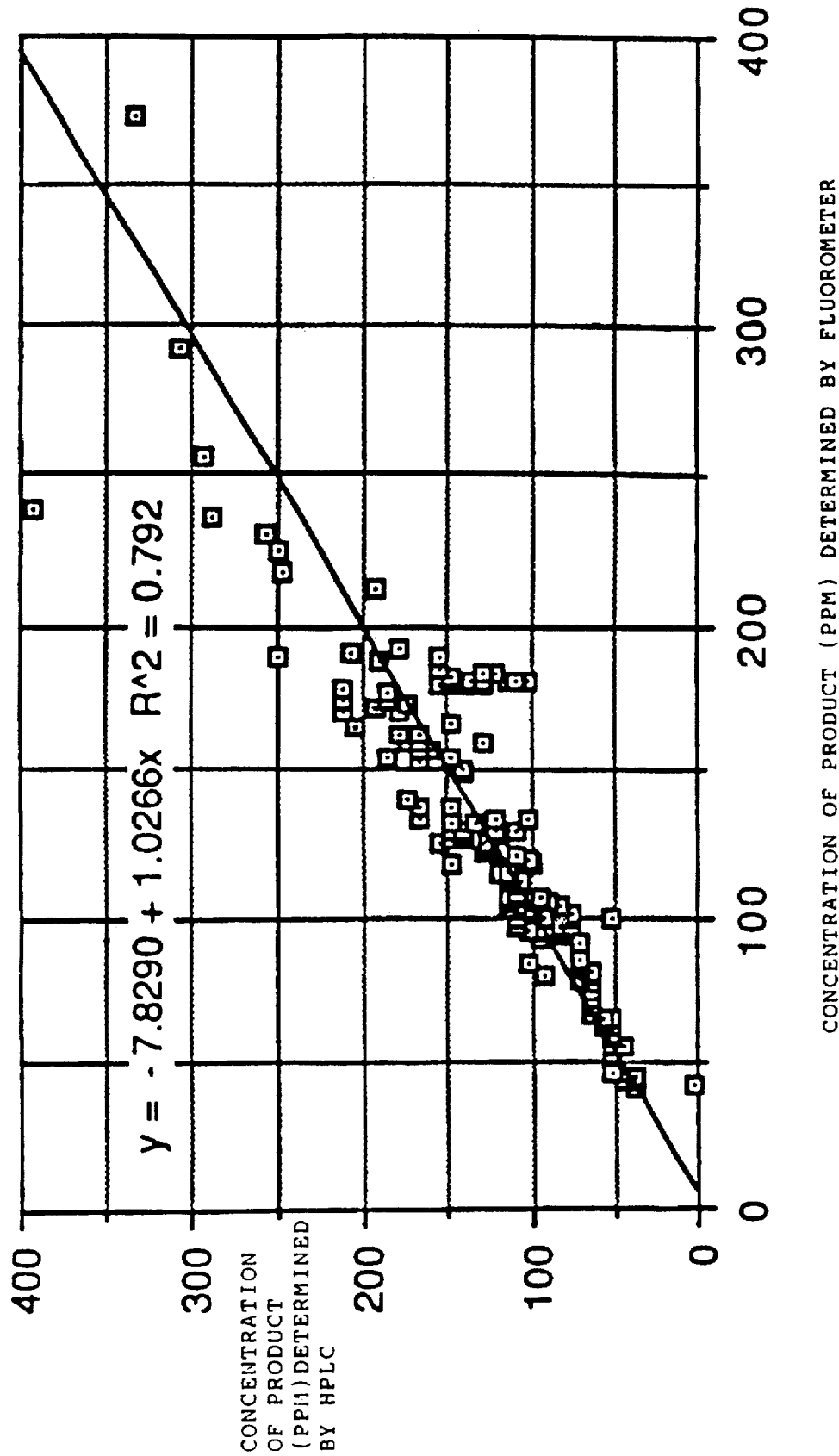
FIG. 4 represents the results of a microbiocide application showing correlation of the substantially inert fluorescent compound and the microbiocide active ingredient.

FIG. 4 represents the results of a microbiocide application in the commercial cooling system referred to previously using the method of the instant invention compared to liquid chromatography measurement. In the Figure, the "x" (horizontal axis) represents ppm of product as determined by the subject invention and the "y" (vertical axis) represents ppm of product as determined by liquid chromatography, of the active biocide ingredient. The Figure shows the excellent correlation between the method using the fluorescent compositions of the subject invention compared to liquid chromatography from a field trial in the commercial cooling system referred to previously.

EXAMPLE III

An industrial cooling tower would be operated using the traced biocide material of Example I. The biocide would be known to be toxic to fish at low dosages. The blowdown of this tower would discharge into a stream containing fish. It would be noted that fish were dying in the stream. The natural presumption would be to blame the operator of the cooling tower, expecting that the microbiocide, or other chemical treatment agents found in the cooling tower blowdown would be responsible for the fish toxicity. Analysis of the stream water by fluorometry would show a normal level of the tracer in the water commensurate with a properly applied biocide program. This analysis would exonerate the owner of the cooling tower system from being responsible for the fish kill.

EXAMPLE IV

An industrial cooling tower would be operated using the traced biocide material of Example I. The blowdown of this tower would discharge into a stream containing fish. It would be noted that fish were dying in the stream. Analysis of the stream water by fluorometry would show a level of tracer indicative of an excess feed of microbiocide into the tower and a corresponding discharge of excess biocide into the stream commensurate with poor biocide management practice. This analysis and a confirming analysis of the stream water for active microbiocide would prove that the owner of the cooling tower system was responsible for the fish kill.

EXAMPLE V

A papermill white water system would be treated with an industrial microbiocide to control the growth of fungi and bacteria. While treatment would have been successful, substantial variation would exist in dosage, and in the application of the microbiocide. To the biocide being fed at the paper mill would be added thereto 0.1% by weight, based on the weight of actives of 1,3,6,8 pyrene tetra sulfonic acid, sodium salt. In addition, a commercial fluorometer capable of providing an excitation wavelength of 365 nm and reading an emission wavelength of 400 nm would be installed in a bypass loop for the water system. Using the system, and controlling the feed of microbiocide by a signal sent to the microbiocide feed pump by the fluorometer, better control of microorganisms would be achieved. In addition, substantial savings would be achieved by the regulation of microbiocide dosage into the system using the compositions and methods of this invention.

EXAMPLE VI

This example demonstrates the efficacy of our invention in the control of zebra mussels using sodium bromide. A midwestern utility would be treating its intake water with a mixture of gaseous chlorine and sodium bromide (forming the hypobromide insitu) for the control of zebra mussels in the water intake system. To the solution of sodium bromide being added to the system would be added 0.1% by weight of 1,3,6,8 pyrene tetra sulfonic acid, sodium salt. A commercial fluorometer would be installed downstream of the water intake. The fluorometer would be set to provide an excitation frequency of 365 nm and read fluorescent emissions of 400 nm. The fluorometer would be connected to an alarm to sound if biocide treatment dropped below a set treatment level. The fluorometer would be calibrated based on normal chemical addition of the bromide salt. In the event the fluorescence level should drop indicating that the feed of sodium bromide feed was interrupted, the alarm would sound thereby allowing plant personnel to correct the feed problem.

EXAMPLE VII

A hotel spa would be controlled by the addition of a solution of hydrogen peroxide as needed to maintain bacteria counts within safe limits. Because of personnel limitations, wet chemical tests for peroxide level would be taken every morning. A commercial fluorometer would be installed into the recycle line of the spa. The fluorometer would be set to activate a pump to supply dilute hydrogen peroxide solution into the system to maintain the system at a designated level of fluorescence. After several days of calibrating the system, the fluorometer would automatically add peroxide when the level of fluorescence indicated that the biocide would be below that required to provide a safe residual level. The process of this invention would allow automation of a previously manual system, and would increase safety by helping to insure that proper biocide would be added.

EXAMPLE VIII

System consumption of biocide is an exceptionally important factor in the application of microbiocontrol chemicals. The composition disclosed in Example I would be fed to a system as described in Example II. The steady-state concentration of biocide would be determined by liquid chromatography and compared to the theoretical steady-state concentration known from the tracer. By use of the mathematical relationship previously given, actual system consumption of the biocide active ingredient would be determined. The cooling system operator then would know quantitatively the degree to which the biocide is being consumed. The operator could then impose a remedy to decrease the system consumption (such as physical cleaning to remove biofilm, chemical neutralization to remove reducing compounds, etc.) and by virtue of attributes of this disclosed invention, the operator would then be able to quantitatively determine the extent to which the remedy had eliminated or removed the undesirable system consumption. This process would significantly reduce the amount of biocide consumed and would therefore lower the volume of biocide used with a resultant decrease in cost. Since biocides are by nature hazardous chemicals, this invention thus would also improve the overall safety of the practice, since less toxic material is required for successful microbiocontrol.

EXAMPLE IX

An open recirculating water cooling system located in a chemical processing plant was dosed with a quantity of the product containing the substantially inert fluorescent compound as disclosed in Example I so as to achieve a concentration of 150 ppm as active microbiocide product. It was observed by measuring the fluorescence of the fluorescent compound in the system discharge (blowdown) that the actual concentration for the first 10 hours of operation was substantially higher than the target dosage added that was based on system capacity and in fact fluorescent measurement showed biocide concentrations well above 250 ppm for several hours. This observation led to the conclusion that the biocide addition point was too close to the blowdown discharge point and that inadequate mixing was taking place during the feed of the microbiocide product. The situation resulted in product waste due to poor distribution since a large amount of product was inadvertently being discharged in the blowdown at the beginning of each slug dose. Because of the ability to determine concentration by fluorescence the operators of the tower became aware of the less than desirable flow distribution at the biocide addition point and were able to take action by moving the biocide addition point to another location in the system where fluorescence

15 measurement indicated that adequate mixing of the biocide with the process stream was occurring. Fluorescence measurement of the water at other points in the system revealed other locations where inadequate mixing was taking place in the system. Substantial cost savings were achieved due to the more efficient application of the biocide.

EXAMPLE X

The use of hydrogen peroxide in pulp and paper applications is an increasingly important application as the use of oxidizing halogen biocides is limited. In one such application, a day tank would be charged with enough $H_2O_2$ (30% by weight aqueous solution) to treat the process for one day. After the tank was filled, a quantity of 1,5-naphthalene disulfonic acid would be added to the tank to achieve a 0.013% by weight concentration of the fluorescent compound. This composition was shown to be stable (>94%) even after 2 days. Similar results were demonstrated for the disodium salt and also with another substantially inert fluorescent compound, 1,3,6,8-pyrene tetrasulfonic acid, tetrasodium salt (used at 0.001 weight percent). The traced hydrogen peroxide solution containing therein the inert fluorescent compound would be useful in the paper making application because, when the contents of the tank were added to the system, there was also by virtue of the invention an inert fluorescent compound added in direct proportion to the oxidant. The distribution of the oxidant throughout the papermaking machine could be readily and quickly measured on a real time basis. System consumption of the oxidant could be determined by comparing the fluorescence level (determining the mount of hydrogen peroxide added and the remaining peroxide) and determining the difference between peroxide added and remaining and calculating the consumption.

The total amount of peroxide added would be determined by fluorescence, and the amount remaining by another technique.

EXAMPLE XI

Stability of various tracers in the presence of biocides was studied over an extended period of time at ambient temperature. The solutions were monitored for the presence of tracers by fluorometer. The results are enumerated in Table I. Fluorescent readings for biocide and tracer formulations are acceptable within the range of 100±5 percent. Some combinations of tracers with biocides produce treatment solutions which are stable over the course of time, while others resulted in an unstable formulation.

The stability of tracers B and C were studied over the course of time in the absence of biocide. Each tracer was monitored independently for more than one year. Fluorescence detection revealed no significant deterioration of either tracer material.

TABLE I

| Formulation Stability Study of Concentrated Biocide + Tracer Compositions | | |
|---|---|---|
| Tracer | Biocide | % Relative Fluorescence |
| B | A | 101% |
| C | A | 102% |
| F | A | X |
| B | D | 102% |
| C | D | 96% |
| F | D | 102% |

TABLE I-continued

| Formulation Stability Study of Concentrated Biocide + Tracer Compositions | | |
|---|---|---|
| Tracer | Biocide | % Relative Fluorescence |
| B | E | 77% |
| C | E | X |
| F | E | 22% |
| G | E | 63% |
| H | E | 96% |
| B | I | X |
| C | I | 52% |
| H | I | 97% |

A = Biocide mixture; aqueous solution of 5-chloro-2-methyl-4-isothiazolin-3-one (1.15%) and 2-methyl-4-isothiazolin-3-one (0.35%)
B = 1,3,6,8 Pyrene tetrasulfonic acid (0.1% aqueous solution)
C = 1,5 Naphthalene disulfonic acid (0.4% aqueous solution)
D = Glutaraldehyde (45% aqueous solution)
E = 2 (Decylthio) ethanamine (15% aqueous solution)
F = 0.1% aqueous solution of fluorescein potassium salt
G = 0.1% aqueous solution of Rhodamine WT
H = 0.1% aqueous solution of 2-Naphthalenesulfonic acid sodium salt
I = Alkyl ($C_{13}$–$C_{15}$) dimethyl benzyl ammonium chloride quat (10%)
X = Could not formulate concentrated biocide + tracer solution

Having thus described our invention, we claim:

1. A method for controlling the feed rate of an aqueous biocide for controlling growth of microbiological organisms into an aqueous system containing said microbiological organisms which comprises the steps of:
   a) adding to said system a known amount of a biocide/inert fluorescent compound combination selected from the group consisting of glutaraldehyde/1,5 naphthalene disulfonic acid, glutaraldehyde/1,3,6,8 pyrene tetrasulfonic acid, mixture of 5-chloro-2-methyl-4-isothiazolin-3-one and 2-methyl-4-isothiazolin-3-one/1,5 naphthalene disulfonic acid, mixture of 5-chloro-2-methyl-4-isothiazolin-3-one/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active biocide in a weight ratio of active biocide to inert fluorescent compound of from 3:1 to 1000:1, said biocide being added at a level to provide a system having a biocide dosage at or slightly greater than the minimum inhibitory concentration for said biocide in the system;
   b) measuring the fluorescence of said inert fluorescent compound; and
   c) maintaining the fluorescence in the system at a constant rate equal to the fluorescence at or slightly greater than the minimum inhibitory concentration of the biocide by adding additional biocide as required.

2. The method of claim 1 wherein from 0.005 to 2.0 percent by weight of the inert fluorescent compound is added based on the weight of active biocide.

3. The method of claim 1 wherein from 0.025 to 1.0 percent by weight of the inert fluorescent compound is added based on the weight of active biocide.

4. The method claim 1 wherein the measurement of the fluorescence of the inert fluorescent compound is continuously monitored by a fluorometer.

5. The method of claim 4 wherein the fluorometer signals a biocide feed pump to turn on in response to levels of fluorescence below a set treatment level, and signals the pump to mm off in response to levels of fluorescence above a set treatment level.

6. The method of claim 1 wherein the aqueous system is selected from the group consisting of recreational water systems, paper mill white water systems, industrial water systems and open recirculating cooling systems.

7. A method for determining the consumption of biocide for controlling growth of microbiological organisms within a fluid system containing said microbiological organisms which comprises the steps of:

a) adding to said fluid system containing microbiological organisms an amount of a composition comprising a biocide/inert fluorescent compound combination of a known weight ratio selected from the group consisting of glutaraldehyde/1,5 naphthalene disulfonic acid, glutaraldehyde/1,3,6,8 pyrene tetrasulfonic acid, mixture of 5-chloro-2-methyl-4-isothiazolin-3-one and 2-methyl-4-isothiazolin-3-one/1,5 naphthalene disulfonic acid, mixture of 5-chloro-2-methyl-4-isothiazolin-3-one and 2-methyl-4-isothiazolin-3-one/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active biocide;

b) determining the amount of biocide added to the system at an initial time by measuring the intensity of the fluorescence of the fluorescent compound present in the system and calculating the mount of biocide using the known weight ratio;

c) determining the amount of biocide present in the system at a second time by measuring the intensity of the fluorescence of the fluorescent compound and calculating the amount of biocide at said second time using the known weight ratio; and d) subtracting the actual amount of biocide present as determined in step (c) from the total amount of biocide added as determined in step (b), which yields the amount of biocide consumed.

8. The method of claim 7 wherein from 0.005 to 2.0 percent by weight of the inert fluorescent compound is added based on the weight of active biocide.

9. The method of claim 7 wherein from 0.025 to 1.0 percent by weight of the inert fluorescent compound is added based on the weight of active biocide.

10. The method of claim 7 wherein the system is an aqueous system.

11. The method of claim 10 wherein the aqueous system is selected from the group consisting of recreational water systems, paper mill white water systems, industrial water systems and open recirculating cooling systems.

12. The method of claim 7 wherein the inert fluorescent compound is added to the biocide at a level to obtain a 0.005 to 1.0% weight percent of the fluorescent compound.

13. A method for maintaining the concentration of a biocide for controlling growth of microbiological organisms in an industrial fluid system containing said microbiological organisms which comprises the steps of:

a) adding to said industrial fluid system containing microbiological organisms an amount of a composition comprising a biocide/inert fluorescent compound combination of a known weight ratio selected from the group consisting of glutaraldehyde/1,5 naphthalene disulfonic acid, glutaraldehyde/1,3,6,8 pyrene tetrasulfonic acid, mixture of 5-chloro-2-methyl-4-isothiazolin-3-one and 2-methyl-4-isothiazolin-3-one/1,5 naphthalene disulfonic acid, mixture of 5-chloro-2-methyl-4-isothiazolin-3-one and 2-methyl-4-isothiazolin-3-one/1,3,6,8 pyrene tetrasulfonic acid, glutaraldehyde/fluorescein, alkyl dimethyl benzyl ammonium chloride quaternary/2-naphthalene sulfonic acid and 2-(decylthio)-ethanamine/2-naphthalene sulfonic acid, wherein said inert fluorescent compound is present in from 0.0005 to 10 percent by weight based on the weight of active biocide;

b) determining the amount of biocide added to the system at an initial time by measuring the intensity of the fluorescence of the inert fluorescent compound present in the system and calculating the amount of biocide using the known weight ratio;

c) determining the amount of biocide present in the system at a second time by measuring the intensity of the fluorescence of the fluorescent compound and calculating the amount of biocide at said second time using the known weight ratio;

d) subtracting the actual amount of biocide present as determined in step (c) from the total amount of biocide added as determined in step (b), which yields the amount of biocide consumed; and e) adding to the industrial fluid system an amount of biocide to maintain the biocide at a specified concentration which inhibits microbial growth.

14. The method of claim 13 wherein from 0.005 to 2.0 percent by weight of the inert fluorescent compound is added based on the weight of active biocide.

15. The method of claim 13 wherein from 0.025 to 1.0 percent by weight of the inert fluorescent compound is added based on the weight of active biocide.

16. The method of claim 13 wherein the industrial fluid system is an aqueous system.

17. The method of claim 16 wherein the aqueous system is selected from the group consisting of recreational water systems, paper mill white water systems and open recirculating cooling systems.

18. The method of claim 13 wherein the inert fluorescent compound is added to the biocide at a level to obtain a 0.005 to 1.0 weight percent of the fluorescent compound based on biocide active ingredients.

* * * * *

UNITED STATES PATENT AND TRADEMARK OFFICE
CERTIFICATE OF CORRECTION

PATENT NO. : 5,702,684
DATED : 12/30/97
INVENTOR(S) : William F. McCoy and John E. Hoots It is certified that error appears in the above-indentified patent and that said Letters Patent is hereby corrected as shown below:

Column 16, Line 36, Claim 1
2-methyl-4-isothiazolin-3-one/1,3,6,8 pyrene

SHOULD READ AS:

-- 2-methyl-4-isothiazolin-3-one and 2-methyl-1-isothiazolin-3-one/1,3,6,8 pyrene --

Column 17, Line 29, Claim 7
system and calculating the mount of biocide using the

SHOULD READ AS:

-- system and calculating the amount of biocide using the --

Signed and Sealed this

Tenth Day of November 1998

Attest:

BRUCE LEHMAN

Attesting Officer

Commissioner of Patents and Trademarks

UNITED STATES PATENT AND TRADEMARK OFFICE
Certificate

Patent No. 5,702,684                  Patented: December 30, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: William F. McCoy, John E. Hoots and Scott A. Borchardt.

Signed and Sealed this Fifteenth Day of December, 1998.

MICHAEL G. WITYSHYN
*Supervisory Patent Examiner*
Patent Examining Art Unit 1651